(12) United States Patent
Sønderberg Frederiksen et al.

(10) Patent No.: US 9,011,855 B2
(45) Date of Patent: Apr. 21, 2015

(54) WEED CONTROL IN JOINTS OF CONCRETE BLOCK AND OTHER PAVING STONE

(76) Inventors: Jens Sønderberg Frederiksen, Svendborg (DK); Poul Konrad Beck, Silkeborg (DK); Steffen Birk Hvorslev, Rødkærsbro (DK)

( * ) Notice: Subject to any disclaimer, the term of this patent is extended or adjusted under 35 U.S.C. 154(b) by 1612 days.

(21) Appl. No.: 10/572,246

(22) PCT Filed: Sep. 17, 2004

(86) PCT No.: PCT/DK2004/000629
§ 371 (c)(1),
(2), (4) Date: Sep. 11, 2006

(87) PCT Pub. No.: WO2005/025316
PCT Pub. Date: Mar. 24, 2005

(65) Prior Publication Data
US 2007/0275857 A1    Nov. 29, 2007

(30) Foreign Application Priority Data
Sep. 17, 2003 (DK) .................... 2003 01347

(51) Int. Cl.
*A01N 55/02* (2006.01)
*A01N 59/00* (2006.01)
*E01H 11/00* (2006.01)
*E01C 5/00* (2006.01)

(52) U.S. Cl.
CPC ............. *E01H 11/00* (2013.01); *A01N 59/00* (2013.01); *E01C 5/003* (2013.01)

(58) Field of Classification Search
CPC ... A01N 59/00; A01N 2300/00; A01N 25/08; E01C 5/003
USPC ............... 424/139.1; 504/187, 189, 320, 367; 514/1.1, 44 R
See application file for complete search history.

(56) References Cited

U.S. PATENT DOCUMENTS 3,499,491 A * 3/1970 Wyant et al. .............. 166/292

FOREIGN PATENT DOCUMENTS

| JP | 05123063 A | * | 5/1993 |
| JP | 06272203 A | * | 9/1994 |
| WO | WO 03037817 A1 | * | 5/2003 |

* cited by examiner

*Primary Examiner* — Janet Epps-Smith
*Assistant Examiner* — Courtney Brown
(74) *Attorney, Agent, or Firm* — James Creighton Wray

(57) ABSTRACT

The present weed reducing material reduces the necessary weed control work by making joint filling sand a hostile substrate for plant and fungus growth by using an environmentally acceptable slow release mineral additive. The additive, having similar grain size distribution, mechanical and rheological properties, forms an integral part of the joint filling sand. The specific gravity of the additive is lower than quartz sand imparting a tendency for the additive to migrate towards the top part of the joint. The additive leads to pore waters rich in sodium and at high pH, both qualities being maintained over long periods. The mixture of additive and sand is handled and applied using conventional laying techniques and equipment, observing usual precautions for mortar or cement mixes with sand. In the environment, reaction with $CO_2$ in the air or in the soil porosity inactivates the causticity, yielding harmless carbonate salts.

15 Claims, No Drawings

WEED CONTROL IN JOINTS OF CONCRETE BLOCK AND OTHER PAVING STONE

BACKGROUND FOR THE INVENTION

This application claims the benefit of Danish Application No. PA 2003 01347 filed Sep. 17, 2003 and PCT/DK2004/000629 filed Sep. 17, 2004, which are hereby incorporated by reference in their entirety.

The present invention concerns a method to obtain weed control properties in joint filling sand through addition of slowly soluble natural minerals or environmentally acceptable industrial wastes.

Joint filling sands are generally used to finish and partly seal the surface of pavements, whether these are made of natural or industrially produced paving stones. The purpose of the joint filling sand is to fill the gaps in the joints, at the same time imparting sufficient load carrying strength to the finished surface, while maintaining its flexibility. As a recurred problem, joint filling sands in general use can also function as substrate for plant and fungus growth. Higher plants, algae and lichens are all strictly considered, weeds (=unwanted plant growth), except in some cases where mosses covering joints can be accepted in relatively old pavements with only moderate traffic, seemingly preventing (other) weeds from getting established. The term weed in this context covers any plant growth in joints. Plant growth in the joint filling causes not only impairment of the appearance of the pavement, but if unchecked can seriously damage the technical functioning of the pavement. Hence it is desirable to develop methods for effective control of weeds in joint filling sands.

To control or prevent weed growth in joint filling sands, commonly applied technologies rely on a multitude of different principles. These include the following control methods alone or in combination: Treatment of the affected area with sodium chloride or other readily soluble salt, treatment of the paved area with weed toxins, mechanical removal, scorching with a flame, electrical or microwave treatment, steaming or sealing the joint using various waxes, resins, or cements forming an impenetrable surface through which weeds cannot get established.

Electrical treatment or microwave treatment is very energy intensive (vide for example Patent application CA2299301) and/or are only effective when applied to seeds under germination. Apart from treatment with toxins, all of the other methods are labour intensive and some methods will to some degree impair the flexibility of the joints and must be repeated at short intervals to be effective. Toxin treatment, being most effective has the disadvantage of being potentially harmful to surrounding vegetation and most effective formulations have inherent acute and long term personnel safety problems and/or can cause pollution of the environment.

BRIEF SUMMARY OF THE INVENTION

The present invention drastically reduces the necessary weed control work by making the joint filling sand a hostile substrate for plant and fungus growth by the use of environmentally acceptable slow release mineral additive. The additive having similar grain size distribution and with similar mechanical and rheological properties forms an integral part of the joint filling sand. In one particular implementation of the invention, the specific gravity of the additive is lower than quartz sand, forming the bulk of the sand, imparting the mixture with an inherent tendency to segregate the additive into the top part of the joint. Once installed, the joint filling sand absorbs moisture from the surrounding soils or by being wetted from above by rain. The resulting hostile environment for weeds is related to a steady slow release from the mineral additive of its sodium constituent, rendering the soil moisture rich in sodium at a high pH, both qualities being maintained over long periods of time. Dry periods will result in up going movement of moisture as experienced in desert climates, leading to a higher concentration of sodium salt and with a higher pH in the top of the joint. This enhances the effectiveness of the joint filling sand in preventing germination of seeds. The whole volume of the joint after infill of the joint sand acts to be effective, preventing plant growth. In wet periods the sodium will be washed down, increasing the sodium concentration as a function of depth causing deeper-rooted weeds to be effected. The high concentration level of sodium and high pH near the surface will be restored to full level when the joint dries up again. The even distribution of the slow release mineral component ensures a constant release of sodium and maintaining a high pH over time also when rain infiltration rates causes flooding of the joint spaces. The overall effect is that weeds are being prevented from germinating and rooted weeds cannot survive with a very limited supply of inorganic nutrients being only sodium (and calcium where concrete block stones are used). The mixture of additive and sand can be handled and applied using conventional laying techniques and equipment, observing usual precautions as used for mortar or cement mixes with sand. In the environment, reaction with $CO_2$ in the air or in the soil porosity will inactivate the causticity, yielding harmless carbonate salts. If mixed with common soil constituents in concentrations less than 10% w/w there is no effect on the plant growth caused by the additive content of the joint filling sand. This means that accidental spills on common garden soil have no significant effect on the fertility of the soil. Another advantage of the present invention is that the active substance being of mineral origin has comparable mechanical properties to the main constituent sand. The additive is chosen from a group of sodium silicate glasses or sodium rich industrial waste glass, which retain its liberation of sodium at a steady rate on exposure to water.

DETAILED DESCRIPTION OF THE INVENTION

State of the Art

When preparing an area for pavement, the generally accepted method calls for removal of unstable soils followed by spreading of multiple layers of sand material(s) imparting the substrate with the required properties for the pavement to be put in place and with the desired functionality. The technology to obtain sufficient strength and other functional properties in the substrate of roads and pathways are well known in the art, vide B-Shackel "Design and construction of interlocking concrete block pavement". School of Civil Engineering, University of New South Wales, Sydney, Australia, ISBN 1-85166-566-8

The pavement itself can be made from a choice of natural and industrially produced flagstones, concrete block stones, cobblestones or other materials suitable for the purpose. Depending on choice of paving stones various laying patterns including adjustment of joint width to give additional strength or attractive appearance is known in the art.

Joint filling sand is used to finish the surface, filling the gap where the paving stones join. A wide variety of joint systems are presently used, depending on area usage and type of paving stone. The most widely used joint fill materials, is however dry or wet sand with a suitable grain size distribution, applied immediately after the paving stone has been laid down. The general requirements to the quality of the joint filling sand can be summarised as follows:

Mechanical strength and cleavage properties of individual sand gains should be close to or equal to that found in sands used for general-purpose building sands or road construction. The strength of the sand grains must be high enough to resist braking down by abrasion forces occurring as a result of load movements in the pavement.

Grain size distribution should be close to values known in the art to give suitable packing of grains and the diameter of the grains must be small enough to allow a free flow into the joints.

Internal frictional properties in the sand, suitable for the purpose

Dry or wet sand according to the preferred compacting technique, used to finish the pavement.

The advantages in this system are related to the very broad range of paving stones, with which it can be used. Furthermore, it is simple to apply and given appropriate compacting after the filling of the joints, it provides a strong enough cohesion between the individual stones for the pavement to function as one plate, yet with an inbuilt flexibility allowing considerable internal movements. Most importantly all these technical properties are obtained at a cheap price. The problem remaining is that the joints fill materials also function as substrates for weeds to grow, this including higher plants, mosses, and lichens.

Weed Abatement Methods for Paved Areas

The weeds can be relatively easy to control using various herbicides and fungicides known in the art, but the adoption of environmentally friendly weed abatement concepts, for both public areas and on private land has made this practice unacceptable. Herbicides and fungicides have caused harmful pollution both in primary receptors of drainage water but also in marine environments a long distance from where the compound was applied. Similarly, various inorganic and readily soluble salts have effect on the occurrence of weeds. Such salts being readily soluble have only effect until washed away; they can have a harmful effect on the concrete, the soil and water close to the application area as well as humans and animals absorbing the salt on to their feet or footwear.

In place of the former practice involving weed abatement with herbicides, various mechanical and thermal techniques have been developed. These new weed abatement practices have in common that they are either ineffective, involves an unacceptable amount of manual labour and energy, and are therefore generally expensive to use.

The thermal methods rely on scorching the weeds by the use of steam, hot air or direct flame, all of these methods consuming unacceptable amounts of energy and labour and the treatment must be repeated at relatively short intervals. In Northern Europe treatment must be performed eight times per season to be effective.

The mechanical methods are less energy intensive but require much manual labour, or are generally not effective, and can even cause considerable damage to the joint system or the paving stones.

Electrical treatment or microwave treatment is very energy intensive, relying on heating up the substrate with the weed. Hence these treatments are costly and must be repeated at regular intervals. A recently developed less energy demanding electrical method, using pulsating high voltage has only effect on germinating seeds (vide for example Patent application CA2299301).

Recently applied joint filling systems overcomes some of these problems by sealing the joints, using wax or resin based sealants. These systems retain the flexibility of the joint and prevent weeds from being established for a period of time. Apart from being difficult to apply with consistent quality in the full depth of the joint, these systems are very expensive, the wax or epoxy additive being prone to break down by sunlight and frost-thaw cycles, and the components used can be harmful to the environment, just like the herbicides.

Thus it is desirable to find a generally applicable method to minimize labour costs and strain on the environment for the abatement of weed growths in paved areas, both on public and private land.

Principles Behind the Invention

All plants take up relatively large amounts of inorganic salts with water from the substrate. By the combination of the uptake of inorganic salts with photosynthesis the plants are able to build organic matter, which in turn is the fundamental basis for higher life. For their metabolism and in order to grow, plants need not only an ample supply of soluble salts but the composition of salts in the soil moisture must allow a sufficient supply of essential elements, major ones being potassium and magnesium salts. Nitrogen and to a certain degree calcium are equally important, as are a number of trace elements. Other common elements, in particular sodium, which can be present in natural environments in relatively high concentrations, have detrimental effects on soil structure as found in normal agricultural soils. This can be observed in desert soils and where mildly saline irrigation water is applied to the land. Excess sodium salt increases the osmotic potential of the soil water (higher salt concentration than in the root sap) and produces conditions that keep the roots from absorbing water, resulting in what is known as physiological drought. This condition arises when the soil water has a higher concentration of soluble ions than the concentration of ions that exist in the sap inside the plant root, making it difficult for the plant to take up water from the soil. Such physiological drought conditions are strongly enhanced by alternating wet and dry periods, because the salt content is increased in the pore waters, when evaporation is greater than infiltration.

The present invention is characterised by achieving the desired weed abatement properties by adding a mineral substance, natural or artificial with a constant, low release of sodium (Na) making this element readily available in the joint sand pore water. Further, the invention is also characterised by ensuring a very low availability of plant essential elements i.e. potassium (K) and magnesium (Mg) in the joint filling sand. This is achieved by using quartz rich sand with a low natural content of the K and Mg as base in the joint filling sand. An additive consisting of a sodium rich glass will serve as a readily available deposit of slow release sodium. This deposit will be activated when rain or any other source of infiltrating water wets the sand. In combination with water, sodium will be released from the glass and at the same time the pH will be above 10. Both of these factors work to inhibit plant growth and germination. In planted areas adjoining the tested paved area, negative effects related to sodium release is absent or drastically reduced.

The joint sand material described in this invention, can be combined with other growth inhibiting factors known in the art. This may include optimisation of grain size distribution to make a compact surface of the joint, enhancing the water repelling properties of all or part of the joint sand by treatment with silicone or other agent with similar effect.

The Functioning of the New Joint Sand

In agricultural science the cat-ionic exchange capacity (CEC) is a measure of the total negative surface charge per mass of soil, which is compensated by interchangeable positive ions. The relative proportion of exchangeable sodium ions to the total CEC value calculated as a percentage defines the Exchangeable Sodium Percentage (ESP). In mathematical terms this means: ESP=(exchangeable Na+×100)/CEC in %. The ESP is related to the solid soil particles. The term describing the actual content of sodium ions in the soil solutions in relation to the essential elements $K^+$ and $Mg^{++}$ is the so-called Sodium Adsorption Ratio (SAR). In mathematical terms, it is defined SAR=Concentration $Na^+$/square root [Concentration $Ca^{++}$+Concentration $Mg^{++}$/]

The solid particles in soil interacts with soil water so that the composition of ions in solution will determine the composition of ions adsorbed to soil ion exchange sites after a period of time. For irrigation water it is known that SAR values greater than 12 will be growth inhibitive for most plants. Similarly, ESP percentages higher than 15% will affect the plant growth significantly (Footnote[1]). Following this learning, the ESP of the joint sand should be greater than at least 15% and the corresponding SAR value should be greater than 12. If quartz sand is chosen as the main joint sand component, the total CEC will be very low. This means that plant roots have to rely on salt uptake directly from the pore water since the supply of exchangeable ions from the substrate is limited. Thus, with a potentially high sodium salt concentration in the pore water of wetted joint sand and the inherent quick drainage after rain, the ESP value becomes less significant and the SAR value becomes the most significant factor determining the survival chances for the plant.

[1] ENVIRONMENTAL HANDBOOK: Environmental Regulations for the Oil & Gas Exploration and Production Industry, Prepared by G. L. Hunt, Environmental Manager. Published by UTAH DIVISION OF OIL, GAS & MINING, State of Utah, Department of Natural Resources January 1996.

In summary, by using joint sand with a very low plant available potassium and magnesium and by adding a constant low release source of sodium, and/or an exchange material with a high load of sodium, a very hostile environment for plants to germinate and grow is established. A disturbing factor, determining the SAR value in joint filling sand has been established as being calcium salt being released from freshly poured concrete and newly made concrete paving stone. For new concrete paving stones, calcium hydroxides emanating from the cement paste will reduce the nominal SAR value to below 12. Despite this, experiments have surprisingly shown that mixtures consisting of quartz sand and additives selected as described below tests have shown that plant (weed) growth will effectively be absent. Germination of for example rap grass seeds on the surface of a bed made from joint filling sand according to the present invention will proceed under favourable conditions. A seed leaf seed leaf is some times produced, but the roots remain on the surface and eventually the plant dies when stoned nutrients in the seed have been used up. This means that a mixture of calcium and sodium ions will prevent weed growth even if the SAR value is lower than specified by the experts in the art. The disturbing effect of calcium in the pore water stemming from the content of calcium hydroxide in freshly made concrete will over time be offset by the carbonatisation that takes place when calcium hydroxide is exposed to atmospheric air, containing CO2. The surface carbonatisation will within a year attain a thickness of about 10 mm (Footnote[2]) effectively sealing the surface and preventing calcium ions from entering into the joint sand pore water. Thus, a high SAR value and a high pH value is re-established in the joint filling sand, provided a steady supply of sodium is maintained.

[2] Nepper-Christensen et al.: Beton-Bogen Cementfabrikkernes tekniske Oplysningskontor. 2. udgave 1985

In the small volume of the joints, the weed preventive effect is neutralised with no harmful effects to the environment by mixing the joint sand into the substrate, if and when the pavement is broken up. The weed abatement property is retained in the joint filling sand (JFS) for mixtures for which the SAR and the ESP values are greater than 12 and 15% respectively. SAR and ESP values for garden and other soils near paved areas are generally very far below the values defined for the present invention, typically less than one tenth or less of the latter values. Therefore more than 90% JFS (dry weight) is required to change the SAR values and ESP values of soil/JFS mixtures to values that are known to affect the plant fertility. Thus, small amounts (less than 10%) JFS mixed with normal soil will have no effect on plant growth. If the joint sand is replaced over time by mechanical degradation the joints can be top filled to renew the weed controlling properties.

The sodium source in the joint fill material is preferably in solid mechanically competent form so that the mechanical properties of the sand are retained. Alternatively, the additive can be in gel or other inconsistent soft form when the combined body of joint sand and additive retain adequate mechanical properties for the satisfactory function of the joint sand.

General Description of Suitable Additives

The additive can be selected from a range of sodium rich natural minerals e.g. sodalite, analcime, sodic nepheline, and other sodium rich, slowly leachable minerals. Further, the additive can be selected from sodium rich, environmentally acceptable industrial wastes, e.g. crushed and appropriately sized glass from used glass containers semi processed sodium rich precursors for mineral or other industrial synthesis or spent sodium ion exchange materials. Apart from having ecologically acceptable properties a suitable additive should possess mechanical strength close to the grains in the natural sand and an ESP value of the ready made joint sand, which is preferably minimum 15%. At the same time the release rate of the sodium from the additive into the pore water of the sand on wetting should result in a SAR value in the pore water preferably greater than 12.

In order to ensure a readily available source of sodium and to preserve the sodium as long as possible in the joint sand, a cat-ion exchange material with the exchange sites filled with sodium may replace part or all of the sodium glass. The cat-ionic exchange material may be chosen from materials low in potassium and magnesium and a high affinity for exchanging sodium into the cat-ionic exchange sites. Suitable materials may be zeolites, clay, humic acid rich organic material, high surface area carbonaceous material or other material with a suitable cat-ionic capacity. All of these materials have different mechanical strength from high silica sand, but can impart an unwanted colour to the finished joint. Furthermore these additives may also change the rheological properties of the joint filling sand.

It should be noted that in actual use the proposed class of additives in the joint filling sand could be combined with other weed reducing measures. Such measures include reduction of capillary pore space in the sand by compacting and or adjustments of grain size distribution. Further possibilities include fining upwards in the grain size distribution of the joint in-fill sand, water repellence induced by surface treatment of the sand, sealing the joint with binder/sealant based on environmentally acceptable waxes or other binding agent.

To avoid the noted disadvantages related to unacceptable colour, steady supply of sodium over time, retention of high pH in the joint, it has been found that the preferred additive is sodium silicate glass. Generally it has been found that most effective agent to obtain all objectives and retain the functioning over a period of up to 10 years, is a mixture of quartz sand and sodium silicate glass.

Effective mixtures are found to be containing more than 0.5% sodium silicate, the balance being quartz sand. To retain the proper functioning and to avoid the mixture being excessively expensive it has been found that the addition of sodium silicate glass should be less than 20% (dry weights).

Effective mixtures of joint filling sands based on quart sand can be made also for concrete stone pavements in which calcium from the concrete lowers the SAR values to below 12. In such circumstances the availability of calcium ions is controlled by the solubility and presence of calcium hydroxide from the concrete paving stones, whereas the presence of sodium ions is controlled by the solubility of sodium silicate glass in the joint filling sand. To make an effective weed-abating joint filling sand the addition of sodium silicate glass should in these cases be higher than 1% dry weight.

Quartz sand and sodium silicate glass are both available as industrial commodities.

EXAMPLES

Quartz sand has a typical CEC value of less than 5 meq/100 g. Since sodium is readily available from the sodium silicate glass and the only soluble or exchangeable cat-ion is sodium. A commercially available sodium silicate glass has a typical composition as follows: SiO2+Na2O min. 99%. Weight ratio SiO2/Na2O=3.25. In water, the material will slowly break down completely, the speed of decomposition being dependant on wetted surface. The chemical reaction is expressed as:

$$\equiv\!SiONa_{glass} + H_2O_{liquid} \Leftrightarrow NaOH_{aq} + \equiv\!SiOH_{glass} \quad \text{(Equation 1)}$$

The pH of the water is a function of the volume to solid ratio, highest pH achieved in smallest possible volume sufficient to wet the surface.

Standard joint sand based on commercially available Danish Tertiary quartz sand was tested to find the content of water at saturation point under conditions where water was allowed free drainage. The water content in the sand mass packed in the same height as in a joint filling was shown to be 16.1% w/w dry solids base.

A test series was carried out using standard quartz joint filling sand with addition of 1% silicate glass and 10% w/w respectively. De-ionised water, simulating rainwater was added to a packed bed of the mixture, the bed being 6 cm in height, which is the most common joint height for cement-based paving stones. The addition of water was adjusted so that the addition was balanced with the drainage thus keeping the bed saturated with water but without causing run off. The number of bed volumes water passing through the bed was recorded and pH was measured at intervals. The test was carried out for an extended period of time over several days with some stops and full drainage.

TABLE 1 pH in quartz joint sand with Na-silicate additive

| pH | 1% additive | 10% additive |
|---|---|---|
| average | 11.17 | 11.77 |
| High | 11.68 | 12.34 |
| Low | 10.76 | 10.50 |
| Count | 31 | 56 |
| Bed volumes | 122 | 116 |

High pH was recorded after stop, this being in accordance with theory, since full drainage gave minimum water volume as compared to each particular mixture's wetted surface.

The above equation 1 for the chemical reaction shows that NaOH is formed when the Na-silicate glass is dissolved and that for each mole $OH^-$, one mole $Na^+$ will be released.

The allowable concentration of Molar concentration of $[Ca^{++}]+[Mg^{++}]$ for the pore waters to retain a SAR value of at least 12 can be calculated from the formula defining SAR as follows: SAR=Concentration$[Na^+]$/square root$[($Concentration$[Ca^{++}]$+Concentration$[Mg^{++}])/2] \Leftrightarrow$ square root$[($Concentration$[Ca^{++}]$+Concentration$[Mg^{++}])/2]$=Concentration $[Na^+]$/SAR $\Leftrightarrow$ Concentration$[Ca^{++}]$+Concentration$[Mg^{++}]$=2*$[$Concentration$[Na^+]$/SAR$]$**2

In above equation "concentration" means "molar concentration"

TABLE 2

SAR values, calculated as function of pH, joint sand mixtures with sodium silicate glass as additive

| pH | [Na$^+$] | SAR | sqrt(([Ca$^{++}$] + [Mg$^{++}$])/2) | ([Ca$^{++}$] + [Mg$^{++}$])/2 | [Ca$^{++}$] + [Mg$^{++}$] |
|---|---|---|---|---|---|
| 10 | 0.0001 | 12 | 8.33E−06 | 6.94E−11 | 1.39E−10 |
| 11 | 0.001 | 12 | 8.33E−05 | 6.94E−09 | 1.39E−08 |
| 12 | 0.01 | 12 | 8.33E−04 | 6.94E−07 | 1.39E−06 |
| 13 | 0.1 | 12 | 8.33E−03 | 6.94E−05 | 1.39E−04 |
| 14 | 1 | 12 | 8.33E−02 | 6.94E−03 | 1.39E−02 |

As explained below, the only other cat-ion present in the pore waters of quartz sand with additive of sodium silicate glass will be Ca$^{++}$ (Footnote[3]), i.e. [Mg$^{++}$] equal or close to 0, the allowable concentration of Ca$^{++}$ to retain a SAR value of 12 in the pore waters, is indicated in the last column to the right in table 2.

[3] stemming from the cement paste of the concrete block

The advantage of using sodium silicate as an additive is, apart from a favourable SAR value also a persistently high pH, which in itself will help to prevent plants from getting established. Actual pH measurements of joint filling sands according to the invention (see table 3 below) after instalment into a pavement consisting of 10 cm by 20 cm concrete paving stones, showed a consistent pH value of about 10.9. A relative high pH of 10.36 was found in quartz joint filling sand (without additive) when recently installed. The high pH is being ascribed to the influence of calcium ions from the cement paste of the concrete paving stones. This effect is reduced as carbonisation forms a skin on the surface of the concrete paving stones.

TABLE 3 pH measurements of joint filling sands

| Age of Pavement | % Na-silicate | pH | Description |
|---|---|---|---|
| 4 months | 0 | 9.33 | Quartz JFS, 10 × 20 cm concrete blocks |
| 15 years | 0 | 8.09 | Unspecified JFS, 10 × 20 cm concrete blocks |
| 6 weeks | 0 | 10.36 | Quartz JFS, 10 × 20 cm concrete blocks, test bed with rap grass growth |
| 6 weeks | 0 | 9.21 | Reference quartz sand, plastic pot, rap grass growth |
| one year | 0 | 8.59 | Quartz JFS, 10 × 20 cm concrete block |

TABLE 3-continued pH measurements of joint filling sands

| Age of Pavement | % Na-silicate | pH | Description |
|---|---|---|---|
| 6 weeks | 0 | 9.40 | Reference quartz sand, 10 × 20 cm, top part of joint, rap grass growth |
| 0 weeks | 6% | 10.90 | Quartz JFS, before application |
| 0 weeks | 0 | 9.44 | Reference quartz sand, before application |
| 6 weeks | 6% | 10.82 | Reference quartz sand, 10 × 20 cm, top part of joint, no weeds |

JFS = Joint Filling Sand

In Northern Europe the annual rainfall is about 80 cm, which means that each square meter receives 800 litres per year. Infiltration into the ground from a paved area has been measured to be about 40% when surface run off and evaporation is deducted. Thus on an annual basis one square meter pavement passes maximum 320 litres rain water through its surface, i.e. through the joint filling sand. For a standard joint of 3 mm width, 60 mm depth and a pavement made up of 10 cm by 20 cm concrete blocks, one square meter pavement requires 4.1 kg joint filling sand. As an example 6% sodium silicate content means that 2.5 mol sodium is available for dissolution per square meter pavement. Based on the pH related sodium solubility shown in table 1, a time related estimate has been made. Assuming infiltration of 320 litres per year per square meter pavement.

TABLE 4

Dissolution scheme for sodium silicate as function of pH

| pH | Mol Na+ | 6% Na-glass | 5% Na-glass | 4% Na-glass |
|---|---|---|---|---|
| | | Litres water required to dissolve all Na-glass contained in joint sand mixture | | |
| 10 | 0.0001 | 25148.3 | 20956.9 | 16765.6 |
| 11 | 0.001 | 2514.8 | 2095.7 | 1676.6 |
| | | Life time for joint filling sand | | |
| 10 | | 78.6 | 65.5 | 52.4 |
| 11 | | 7.9 | 6.5 | 5.2 |

The dissolution values calculated for of all sodium silicate glass to be removed from the joint sand mixtures at varying additive strength. In actual case, in situ measurements of pH in finished pavements of concrete block with 6% additive showed a pH of between 10.5 and 10.9, indicating a lifetime for full functioning of the joint filling sand to be between 7.8 and 22 years. This calculation does not account for top maintenance filling at intervals when/if joint sand has been physically removed.

Weed Tests

Various mixtures were tested for germination and growth for an extended period under lab conditions with 12 hours artificial light (fluorescent daylight tube) and 12 hours dark. The bed was prepared in 8 cm diameter plastic flowerpots with 6 cm infill of the test material. Watering was carried out at intervals, so as to keep the bed from drying out at all times. In each bed 50 seeds of rape grass were spread out evenly and the bed was exposed to light as explained. The numbers of germinated seeds were recorded in each bed as depicted in table below:

TABLE 5 weed test with a selection of additives
Germinating seeds, rape grass

| Mixture | 20 Nov | 25 Nov | 26 Nov | 27 Nov | 28 Nov | 29 Nov | 02 Dec | 03 Dec | 04 Dec | 06 Dec | 08 Dec |
|---|---|---|---|---|---|---|---|---|---|---|---|
| Quartz sand | 0 | 16 | 19 | 25 | 28 | 30 | 34 | 38 | 37 | 36 | 38 |
| 5% sodalite | 0 | 1 | 4 | 7 | 8 | 10 | 12 | 9 | 11 | 13 | 11 |
| 10% sodalite | 0 | 0 | 0 | 0 | 0 | 0 | 0 | 0 | 0 | 0 | 0 |
| 20% sodalite | 0 | 0 | 0 | 0 | 0 | 0 | 0 | 0 | 0 | 0 | 0 |
| Quartz sand | 0 | 18 | 25 | 30 | 30 | 34 | 36 | 37 | 36 | 38 | 36 |
| 5% olivine | 0 | 4 | 5 | 11 | 14 | 14 | 18 | 19 | 14 | 21 | 18 |
| 10% olivine | 0 | 4 | 5 | 5 | 10 | 7 | 14 | 9 | 12 | 14 | 15 |
| 20% olivine | 0 | 5 | 5 | 14 | 16 | 16 | 20 | 17 | 19 | 24 | 21 |
| Quartz sand | 0 | 23 | 28 | 30 | 34 | 37 | 41 | 43 | 41 | 42 | 39 |
| 5% glauconite | 0 | 15 | 17 | 25 | 26 | 29 | 29 | 33 | 28 | 30 | 33 |
| 10% glauconite | 0 | 1 | 8 | 13 | 15 | 20 | 17 | 19 | 17 | 20 | 22 |
| 20% glauconite | 0 | 0 | 0 | 6 | 10 | 15 | 13 | 16 | 19 | 23 | 29 |
| Quartz sand | 0 | 16 | 24 | 27 | 31 | 35 | 37 | 39 | 38 | 37 | 36 |
| 5% glass | 0 | 0 | 0 | 0 | 0 | 0 | 0 | 0 | 0 | 0 | 0 |
| 10% glass | 0 | 0 | 0 | 0 | 0 | 0 | 0 | 0 | 0 | 0 | 0 |
| 20% glass | 0 | 0 | 0 | 0 | 0 | 0 | 0 | 0 | 0 | 0 | 0 |

"Quartz sand" in above table 5 refers to standard quartz joint filling sand.

A similar test with 1% Na-silicate additive under similar conditions gave no germination in the pots with additive but up to 25 in standard quartz joint sand without additive.

Rape grass and dandelion is the most frequent and easily established weed in joint fillings.

Results of germination tests in various growth media as compared to sand prepared according to this invention is depicted in table 6 below.

TABLE 6

Weed germination test. (JFS = Joint Filling Sand, 6% = 6% sodium silicate glass) Weed germination test (18 days)

| Plant | Growth media | Average no shoots | Average germination percentage (standard deviation) | Plant size on count |
|---|---|---|---|---|
| Annual Rape grass | 0-1 mm Quartz sand | 141 | 70.3 (7.8) | 2 leaves |
| | 0-1 mm JFS, 6% | 0 | 0.0 (0.0) | — |
| | 0-3.5 mm quartz sand | 152 | 76.2 (8.5) | 2 leaves |
| | 0-3.5 mm JFS, 6% | 0 | 0.0 (0.0) | — |
| | Peat moss growth media | 175 | 87.7 (4.3) | 2 leaves |
| Dandelion | 0-1 mm Quartz sand | 140 | 69.8 (3.2) | 2-3 leaves |
| | 0-1 mm JFS, 6% | 0 | 0.0 (0.0) | — |
| | 0-3.5 mm quartz sand | 142 | 70.8 (4.9) | 2-3 leaves |
| | 0-3.5 mm JFS, 6% | 0 | 0.0 (0.0) | — |
| | Peat moss growth media | 110 | 54.8 (3.4) | 4-5 leaves |
| Weed species: | Annual rape grass (*Poa annua*) | | Dandelion (*Taraxacum officinale*) | |

DISCLOSURE OF THE INVENTION

It is an object of the invention to provide an environmentally acceptable joint filling mixture, which does not allow weed to grow in the joints over an extended period of time, such as 5 years.

It is an object of the invention to provide a mixture, which has an inhibiting effect on plant growth.

It is an object of the invention to provide a joint filling mixture, which can be used with a very broad range of paving stones.

It is an object of the invention to provide a joint filling mixture, which is simple to apply, gives appropriate compacting after the filling of the joints, provides a strong enough cohesion between the individual stones for the pavement to function as one plate, yet provides an inbuilt flexibility allowing considerable internal movements.

It is an object of the invention to provide a cheap joint filling mixture.

It is the object of the invention to provide a joint filling mixture with acceptable colour, matching the paving stone.

These objects are achieved by the following embodiments.

In one embodiment a mixture according to claim 1 is provided.

The term "pavements and the like" is defined as a surface construction made of paving stones, where the paving stones are joined together resulting in joints between pairs of neighbouring paving stones. The pavement stones can be made from a choice of natural and industrially produced stone materials, such as flagstones, concrete block stones, cobblestones, granite blocks or other materials suitable for the purpose.

The sand may be naturally occurring quartz sand, in which the individual mineral grains is dominated by quartz, defined as a mineral in which silicon atoms are connected by oxygen atoms in a complex structure. The sand may have naturally occurring impurities. Silt may also be used bearing in mind that the difference between sand and silt is accorded to a difference in particle size, silt having the smaller size of the two. The sand preferably has a low content of potassium $K^+$ and magnesium $Mg^{2+}$. The sand may also be a mixture of quartz sand and one or more non-quartz sands. In this context the term quartz sand is used to define elastic sediment containing more than 90% quartz and a grain size 0.06 mm to 2 mm, being a generally accepted grading for people skilled in the art of geology. In industry this rigid grain size scheme is somewhat looser, generally allowing about 5% sizes outside the defined range, i.e. 5% finer than 0.06 and 5% coarser than 2 mm. Thus, in general technical use, sands for which 90% of the grain sizes fall within the above boundaries, is accepted as sand.

The "sustained release of sodium" means that sodium is released from the sodium containing substance to an aqueous phase in contact with the sodium containing substance at a controlled rate over an emended period of time. The sodium has an inhibiting effect on plant growth. A "controlled rate" means that the concentration of sodium in the aqueous phase is maintained within desired limits over the extended period of time. The "desired limits" are the limit within the concentration of sodium in the aqueous phase is herbicidally effective, thus preventing weed to grow.

The extended period of time may be at least 2 years, such as at least 3 years such as at least 5 years, such as at least 10 years, such as at least 20 years.

The sodium containing substance is particulate and may have a particle size comparable to the sand particle size. The mixture may be saturated with an aqueous phase. A "water saturated mixture" is defined as a mixture wetted with water, where the mixture cannot be wetted further without resulting in infiltration and excess water flushing through the mixture. The water in a water-saturated mixture is typically present as pore water between the particulates of the mixture.

In one embodiment a mixture according to claim 2 is provided.

In one embodiment a mixture according to claim 3 is provided.

A joint fitting mixture according to claim 1 and 2, where the molar concentration of calcium ions [$Ca^{++}$] is 2.5E-02 or less Surprisingly experiments showed that even for mixtures to which calcium was present in balance with solid calcium hydroxide i.e. calcium concentration is saturated as a result of calcium hydroxide being washed out from the cement paste of concrete paving stones the joint filling sand with additive according to this invention plant growth was inhibited.

In one embodiment a mixture according to claim 4 is provided.

In one embodiment a mixture according to claim 5 is provided.

Claim 4 and 5 is related to specification of appropriate SAR and ESP values for which definitions are found in the body of the text.

In one embodiment a mixture according to claim 6 is provided.

The allowable amount of additive is dictated by economic considerations and retention of environmentally acceptable amounts of sodium release to surrounding soils.

In one embodiment a mixture according to claim 7 is provided.

In one embodiment a mixture according to claim 8 is provided.

A joint filling mixture according to any of the above claims, where the sodium containing substance comprises one or more substances selected from the group consisting of
sodium containing silicates,
such as one or more sodic feldspatoids,
such as the sodic feldspatoids selected from the group consisting of sodalites, analcimes, sodic nepheline,
Other industrially derived glasses or wastes essentially having a chemical composition as the natural minerals or calcium silicate glass The sodium containing substances may be a rock material, or a mineral. A rock material of silicate origin is preferred due to the abundance (about 90% of the earth's crust is silicate) and due to the compatibility with soils in which mineral substances make up very substantial parts. A silicate capable of releasing sodium ions into a water phase is used among the many silicates found in nature.

In many sectors of industry, various glass products have a composition as varieties of calcium silicate glass known since ancient times and used in products such as flat glass for windows or container glass for bottles. Glassy slags from power stations, steel works or similar slag producing processes are known and have chemistries according to the actual process.

In one embodiment a mixture according to claim 10 is provided.

A joint filling mixture according to preceding claim, where the sodium containing substance is sodalite and the mass relationship, stated as mass (sodalites)/mass (sand) is between 0.5/99.5 and 10/90, such as between 1/99 and 5/95

This mixture represents a preferred embodiment of the invention. The sodalites and the quartz sand may contain impurities. The socialites may be one or more of: hauyne, lazurite, nosean, sodalite.

In one embodiment a mixture according to claim 11 is provided.

A joint filling mixture according to any of the above claims, where the sodium containing substance comprises one or more substances selected from the group consisting of sodium silicate glasses This mixture represents a more preferred embodiment of the invention.

This group of glasses consist of various proportions of sodium bound in a complex silicate network in various molar proportions $SiO_2/Na_2O$. A sodium containing glass may be used such as sodium silicate glass comprising water glass, soluble glass, silicate of soda, sodium orthocilicate, silicic acid sodium salt. Sodium silicate glass has the nominal structure of $Na_4O_4Si$ and may contain impurities.

Other cations than sodium acceptable in this group of glasses is aluminium and iron, whereas glasses containing $Mg^{++}$, $Ca^{++}$, and $K+$ is accepted only where these elements will not change the SAR and ESP values.

In one embodiment a mixture according to claim 12 is provided.

A joint filling mixture according to preceding claims, where the sodium containing substance is sodium silicate glass and the mass relationship, stated as mass (sodium silicate glass)/mass (sand) is between 0.5/99.5 and 10/90, such as between 1/99 and 5/95.

This mixture represents most preferred embodiment of the invention.

In one embodiment a mixture according to claim 13 is provided.

A joint filling mixture according to any of the above claims, where the sodium containing substance comprises one or more cat-ionic exchange materials selected from the group consisting of zeolites, clays, organic materials comprising humic acid, ion-exchange polymeric materials, high surface area carbonaceous materials, which cat-ionic exchange materials comprises exchange sites with $Na^+$.

The cat-ionic exchange materials may be naturally occurring or artificially manufactured materials. The naturally occurring materials include zeolites, clays, aluminium silicates, and organic materials comprising humic acid and high surface area carbonaceous materials. Artificially cat-ionic exchange materials may be ion-exchange polymeric materials which are polymeric materials, mixtures, and compositions which can be converted to ion-exchange materials by chemical reactions, as well as mixtures of materials at least one of which is an ion-exchange material or is capable of forming an ion-exchange material and wherein the intent is to form an ion-exchange material. Typical cationic groups thereby forming cationic, ion-exchange polymeric materials are: Sulfonic acid ($-SO_3H$), carboxylic acid ($-COOH$), hydroxyl ($-OH$), phosphoric ($-PO_3H_2$) groups. The polymeric material may be a resin such as polystyrene with a large surface.

The cat-ionic exchange material may be chosen from materials low in calcium and magnesium, and may also have a high affinity for exchanging sodium into the cat-ionic exchange sites. The cat-ionic exchange material comprises exchange sites with sodium ions, which may be naturally occurring or may be substituted into the exchange sites artificially.

A mixture according to claim 13 ensures ample supply of sodium and at the same time a very low availability of calcium, magnesium and other essential elements for plant growth.

In one embodiment a mixture according to claim 14 is provided.

A joint filling mixture according to any of the above claims, where the sand is a mixture of a quartz sand and one or more non-quartz sand(s) and where the mass relationship stated as mass (quartz sand)/mass (sand), is 70/30 or more, such as 90/10 or more, such as 95/5 or more, such as 99/1 or more, such as 99.9/1 or more.

In one embodiment a mixture according to claim 15 is provided.

A joint filling mixture according to any of the above claims, where the mean particle size of the sand is between 0.05 mm and 5 mm, such as between 0.05 mm and 3 mm, between 0.05 mm and 2 mm, between 0.05 mm and 1 mm, In one embodiment the use of a mixture according to any of claims 1-15 is provided for weed control.

Use of a joint filling mixture according to any of claims 1-15 for weed control.

In other aspects of the invention joint filling techniques may be employed, such as:
optimisation of grain size distribution to make a compact surface of the joint,
enhancing the water repelling properties of all or part of the joint sand by treatment with silicone or other agent with similar effect.

The invention claimed is:

1. A herbicidally effective weed control pavement joint filling loose granular sand mixture, which is not a mortar or cement mixture, consisting essentially of a granular sand mixture of quartz sand and at least one sodium containing substance selected from sodalite or silicate containing glass, wherein a concentration of sodium formed in an aqueous phase of the sodium containing substance for providing sustained release of sodium in the aqueous phase and filling pores of the joint filling granular mixture when wetted by rain water, wherein a ratio of a mass of sodium containing substance mass of sand is between 0.5/99.5 and 10/90, wherein the pavement joint filling loose granular mixture retains loose granularity after application to desired pavement joints.

2. The mixture of claim 1, wherein the herbicidally effective concentration of sodium in the aqueous phase comprises a molar concentration of sodium ions $[NA^+]$.

3. The mixture of claim 1, wherein sodium containing substance providing the molar concentration of sodium ions is selected from the group consisting of sodium containing substances providing in the aqueous phase molar concentrations of $[NA^{+]\ is}\ 10^{-3}$ or more, $[NA^{+]\ is}\ 10^{-4}$ or more, $[NA^{+]\ is}\ 10^{-5}$ or more, or $[NA^{+]\ is}\ 10^{-6}$ or more, and combinations thereof.

4. The mixture of claim 1, wherein the sodium containing substance produces a molar concentration of calcium ions $[Ca^{++}]$ is 2.5E-02 or less.

5. The mixture of claim 1, wherein the joint filling granular mixture comprises an initial sodium absorption rate value in the aqueous phase selected from the group consisting of granular mixtures having initial sodium absorption rates of 10 or more, 12 or more, 14 or more, and combinations thereof.

6. The mixture of claim 1, wherein the mass ratio of mass of sodium containing substances/mass of sand is selected from the group consisting of between 1/99 and 5/95.

7. The mixture of claim 1, wherein the joint filling granular mixture comprises a pH value in the aqueous phase selected from the group consisting of 9 or more, 10 or more, 12 or more, and combinations thereof.

8. The mixture of claim 1, wherein sodium release is sustained for number of years selected from the group consisting of more than 2 years, more than 5 years, more than 10 years, and combinations thereof.

9. The mixture of claim 1, wherein the silica containing glass is industrially derived glasses or wastes essentially having a chemical composition similar to the natural minerals or calcium silicate glass.

10. The mixture of claim 1, wherein mean particle size of the sand is selected from the group consisting of sizes between 0.05 mm and 5 mm, between 0.05 mm and 3 mm, between 0.05 mm and 2 mm, between 0.05 mm and 1 mm and combinations thereof.

11. A joint filling mixture, which is not a mortar or cement mixture, consisting of between 99.5% and 90% sand and between 0.5% and 10% at least one sodium containing substance selected from sodalite or silicate containing glass, said sodium containing substance providing sustained release of sodium to an aqueous phase in contact with the sodium containing substance and the joint filling mixture having an initial Sodium Adsorption Ratio (SAR) value in the aqueous phase of 10 or more, such that a herbicidally effective concentration of sodium in the aqueous phase filling the pores of the joint filling sand is present when the joint filling mixture is wetted by rain water, wherein the pavement joint filling loose granular mixture retains loose granularity after application to desired pavement joints.

12. The joint filling mixture according to claim 11, wherein the SAR value in the aqueous phase is 12 or more.

13. The joint filling mixture according to claim 11, where the herbicidally effective concentration of sodium in the aqueous phase sated as the molar concentration of sodium ions, $[Na+]$ is $10^{-3}$ or more.

14. The joint filling mixture according to claim 11, comprising a molar concentration of calcium ions $[Ca++]$ of 2.5E-02 or less.

15. The joint filling mixture according to claim 11, where the joint filling mixture has an Exchangeable Sodium Percentage (ESP) value of 12% or more.

* * * * *